United States Patent [19]

Brouwer

[11] 4,310,432
[45] * Jan. 12, 1982

[54] LIQUID SOAP COMPOSITION

[75] Inventor: Hendrik W. Brouwer, Vlaardingen, Netherlands

[73] Assignee: Lever Brothers Company, New York, N.Y.

[*] Notice: The portion of the term of this patent subsequent to Dec. 27, 1994, has been disclaimed.

[21] Appl. No.: 912,700

[22] Filed: Jun. 5, 1978

Related U.S. Application Data

[63] Continuation of Ser. No. 839,534, Oct. 5, 1977, abandoned, which is a continuation of Ser. No. 714,450, Aug. 16, 1976, Pat. No. 4,065,398, which is a continuation of Ser. No. 641,203, Dec. 16, 1975, abandoned, which is a continuation of Ser. No. 450,533, Mar. 12, 1974, abandoned.

[30] Foreign Application Priority Data

Mar. 15, 1973 [GB] United Kingdom ............... 12513/73
Sep. 24, 1973 [GB] United Kingdom ............... 44624/73

[51] Int. Cl.$^3$ .......................... C11D 9/00; C11D 9/14; C11D 9/30; C11D 17/08
[52] U.S. Cl. ................... 252/108; 252/109; 252/117; 252/173; 252/367; 252/368; 252/DIG. 14
[58] Field of Search ............... 252/108, 111, 112, 118, 252/122, 124, 173, DIG. 14, 109, 117

[56] References Cited

U.S. PATENT DOCUMENTS

2,792,347  5/1957  Stegemeyer .......................... 252/108

OTHER PUBLICATIONS

*Cosmetics–Science & Technology*, Ed. by E. Sagarin, Interscience Publishers, Inc., New York 1957, pp. 387–392.
Wm. R. Keithler: "The Clear Shampoo", *Drug & Cosmetic Ind.*, vol. 75, pp. 610, 611 & 710–714, Nov. 1954.

*Primary Examiner*—Dennis L. Albrecht
*Attorney, Agent, or Firm*—Melvin H. Kurtz

[57] ABSTRACT

Stable concentrated aqueous liquid soap solutions containing up to 50%, and possibly higher, by weight of sodium soap can be obtained, if the soap comprises a mixture of at least one sodium soap (A) derived from $C_8$–$C_{14}$ saturated fatty acids and at least one sodium soap (B) derived from $C_{16}$–$C_{22}$ mono- and/or di-unsaturated fatty acids, in which the ratio by weight of soap (A) to soap (B) is within the range of 9:1 to 1:9.

2 Claims, No Drawings

LIQUID SOAP COMPOSITION

This application is a continuation of application Ser. No. 839,534, filed Oct. 5, 1977, now abandoned, which, in turn, is a continuation of application Ser. No. 714,450, filed Aug. 16, 1976, now U.S. Pat. No. 4,065,398, which, in turn, is a continuation of application Ser. No. 641,203, filed Dec. 16, 1975, now abandoned, which, in turn, is a continuation of application Ser. No. 450,533, filed Mar. 12, 1974, now abandoned.

This invention relates to soap compositions and more particularly to sodium soap compositions that will form highly concentrated aqueous liquid solutions and to highly concentrated aqueous liquid solutions formed from said sodium soap compositions.

Liquid concentrated sodium soap solutions are useful for the preparation of stock solutions, e.g. in the laundry industries, in the textile industries; for the compounding of liquid detergent compositions, hand and body cleansers and possibly for various other applications. In terms of economy a highly concentrated solution is of considerable advantage but hitherto it has not been possible to produce a really concentrated sodium soap solution in the form of a pourable liquid that can be handled without difficulty at room temperature.

It has been suggested to use viscosity reducing agents, such as alkyl oleates, mineral oils and emulsifying agents, by which according to U.S. Pat. No. 2,676,152 solutions have been obtained which contain 20% by weight of sodium oleate. Experiments have shown, however, that pure sodium oleate and water at a concentration of 20% by weight is a solid mass. Addition of 2% butyl oleate did not change the consistency of the system.

It has now been found that stable concentrated aqueous liquid soap solutions containing up to 50%, and possibly higher, by weight of sodium soap can be obtained, if the soap comprises a mixture of at least one sodium soap (A) derived from $C_8$–$C_{14}$ saturated fatty acids and at least one sodium soap (B) derived from $C_{16}$–$C_{22}$ mono- and/or di-unsaturated fatty acids, in which the ratio by weight of soap (A) to soap (B) is within the range of 9:1 to 1:9.

Accordingly, the invention provides a soap composition comprising essentially a mixture of (A) at least one sodium soap of $C_8$–$C_{14}$ saturated fatty acids and (B) at least one sodium soap of $C_{16}$–$C_{22}$ mono- and/or di-unsaturated fatty acids, in a weight ratio of from 9:1 to 1:9.

The invention further provides an aqueous liquid solution of a soap composition comprising essentially (A) at least one sodium soap of $C_8$–$C_{14}$ saturated fatty acids and (B) at least one sodium soap of $C_{16}$–$C_{22}$ mono- and/or di-unsaturated fatty acids, wherein soap (A) and soap (B) are present in a weight ratio of from 9:1 to 1:9.

Examples of suitable sources of $C_8$–$C_{14}$ saturated fatty acids for use in the invention are pure or technical grades of commercially available myristic acid, lauric acid, capric acid, caprylic acid, coconut and palm-kernel fatty acids, and mixtures thereof.

Examples of suitable sources of $C_{16}$–$C_{22}$ mono- and/or di-unsaturated fatty acids for use in the invention are pure or technical grades of commercially available oleic acid, ricinoleic acid, fatty acids derived from castor oil and from rapeseed oil, and mixtures thereof.

The term unsaturated fatty acids used herein includes hydroxy unsaturated fatty acids.

According to the invention it has been established that to some extent the fatty acid chain length distribution and also the presence of other fatty acid soaps in both soap (A) and soap (B) influence the solubility of the soap composition. Generally it can be said that the amount of other fatty acid soaps present should not be higher than 20% by weight of the soap composition.

If necessary other surface active agents may be incorporated as well in such proportions that the solubility of the soap is not substantially influenced by the composition. Examples of such other surface active agents known in the art are alkylbenzene sulphonates, alkane sulphonates, alkene sulphonates, alkyl sulphates, alkylether sulphates, polyoxyethylene condensation products of primary or secondary alcohols, polyethylene oxide condensation products of alkylphenols, fatty acid amides, and block polymers of ethylene oxide and propylene oxide.

Preferably, soap (A) is derived from saturated $C_8$–$C_{14}$ fatty acids having a proportion of $C_8$–$C_{12}$ fatty acids of more than 50% by weight and soap (B) is derived from mono- and/or di-unsaturated $C_{16}$–$C_{22}$ fatty acids having a proportion of $C_{18}$ unsaturated fatty acids of more than 50% by weight. For these types of soap the optimum ratio lies within the range of about 4:1 to 1:4.

By using the invention highly concentrated aqueous soap solutions containing at least 20% by weight of sodium soap can be obtained which remain stable in the form of a pourable liquid at room temperature. It is thus clear that such highly concentrated soap solutions show considerable advantages over diluted or less concentrated solutions with respect to transport and storage facilities.

The liquid soap solution of the invention may, if desired, contain other usual adjuncts in minor amounts for adaptation to its purpose of use or to improve its properties. Examples of such adjuncts are colouring agents, perfumes, bacteriostats, soil-suspending agents, anti-oxidants, lather boosters and preserving agents.

Furthermore detergency builders and sequestering agents, such as the alkalimetal tripolyphosphates, alkalimetal pyrophosphates, alkalimetal nitrilotriacetate, ethylene-diamine tetraacetate, ethylene-diamine tetraphosphonate etc., which are incorporable in the liquid soap solution in adequate amounts without causing phase separation.

The soap solution according to the invention can be prepared by normal saponification of the selected fatty acid mixture with caustic alkali and diluting the soap mass as desired with the required amount of water.

The following Examples will illustrate the invention, the percentages being by weight, unless otherwise indicated.

EXAMPLE I

In a 200 liter crutcher a mixture of 61.5% oleic acid ("White olein 7203", a commercial product ex Unilever-Emery N.V.) and 38.5% lauric acid ("Lauric acid 6932", a commercial product ex Unilever-Emery N.V.) was neutralised with a solution of 30% NaOH. Live steam was led in during the neutralisation process. The mass was salted out with NaOH and separated. After the lye was discarded, the soap mass was neutralised to neutral reaction with a small amount of fatty acid.

Finally the soap mass was diluted with water containing a small amount of a preserving agent, until a clear liquid product was obtained which remained liquid on standing. The aqueous liquid concentrate on analyzing contained 40% of sodium soap, consisting of 39% $C_{10}$-$C_{14}$ saturated fatty acid soap, 4% $C_{16}$-$C_{18}$ saturated fatty acid soap and 57% $C_{16}$-$C_{18}$ unsaturated fatty acid soap.

| Specification of fatty acids used: | White olein 7203 | Lauric acid 6932 |
|---|---|---|
| Titer | 6° C. | 40.5–42° C. |
| Acid number | 197–203 | 277–282 |
| Saponification number | 195–205 | 277–282 |
| Iodine number | 90–96 | <0.5 |
| Unsaponifiable | <2% | traces |
| Fatty acid chain length distribution | 7203 | 6932 |
| $C_{10}$ | — | 3 |
| $C_{12}$ | 0.5 | 92 |
| $C_{14}$ | 3.0 | 5 |
| $C_{16}$ | 4.0 | — |
| $C_{16}'$ | 6.0 | — |
| $C_{18}$ | 0.5 | — |
| $C_{18}'$ | 73.0 | — |
| $C_{18}''$ | 8.0 | — |

EXAMPLES II-III

By the method of Example I soap solutions containing 45% of the following sodium soap mixtures were made:

II (a) A mixture of 30% technical grade oleic acid and 70% technical grade capric acid soaps.
(b) A mixture of 45% technical grade oleic acid and 55% technical grade capric acid soaps.

III (a) A mixture of 20% technical grade oleic acid and 80% technical grade caprylic acid soaps.
(b) A mixture of 35% technical grade oleic acid and 65% technical grade caprylic acid soaps.

All these soap solutions were easily pourable liquids at 20°–25° C. and remained stable on standing.

EXAMPLES IV-V

Liquid solutions containing 40% soap were obtained from the following soap mixtures:

IV (a) 75/25 sodium oleate/sodium caprate.
(b) 85/15 sodium oleate/sodium caprate.

V

85/15 sodium oleate/sodium $C_9$-fatty acid soap. These soap solutions were easily pourable liquids at 20° C. and remained stable on standing.

EXAMPLES VI-X

The present Examples demonstrate further highly concentrated liquid sodium soap solutions from various systems.

| | | Fatty acid system | Na-soap ratio | Na-soap concentration |
|---|---|---|---|---|
| VI | | White olein/coconut f.a. | 60:40 | 40% |
| VII | a. | Rapeseed oil f.a./lauric acid | 60:40 | 38% |
| | b. | Rapeseed oil f.a./lauric acid | 45:55 | 40% |
| | c. | Rapeseed oil f.a./lauric acid | 30:70 | 40% |
| VIII | a. | Rapeseed oil f.a./coconut f.a. | 60:40 | 45% |
| | b. | Rapeseed oil f.a./coconut f.a. | 45:55 | 45% |
| | c. | Rapeseed oil f.a./coconut f.a. | 30:70 | 40% |
| IX | a. | Castor oil f.a./lauric acid | 60:40 | 45% |
| | b. | Castor oil f.a./lauric acid | 45:55 | 38% |
| | c. | Castor oil f.a./lauric acid | 75:25 | 45% |
| X | a. | Castor f.a./coconut f.a. | 60:40 | 40% |
| | b. | Castor f.a./coconut f.a. | 45:55 | 35% |
| | c. | Castor f.a./coconut f.a. | 75:25 | 45% |

The fatty acid distribution of the raw materials used in the systems is given in the table below.

TABLE

| | Chain length | Lauric acid | White olein | Coconut oil | Castor oil | Rapeseed oil |
|---|---|---|---|---|---|---|
| Caprylic acid | C 8 | | | 6.3 | | |
| Capric acid | C 10 | | | 5.8 | | |
| Lauric acid | C 12 | 99.5 | 0.7 | 48.5 | | |
| Myristic acid | C 14 | 0.3 | 4.3 | 18.5 | | 0.1 |
| Palmitic acid | C 16 | 0.2 | 6.6 | 9.0 | 1.5 | 5.4 |
| Palmitic acid, mono-unsaturated | C 16 | | 6.8 | | | 0.3 |
| Stearic acid | C 18 | | 1.0 | 2.5 | 1.4 | 1.9 |
| Oleic acid | C 18 | | 66.2 | 6.9 | 4.0 | 33.0 |
| Linoleic acid | C 18 | | 9.5 | 2.3 | 3.6 | 14.6 |
| Linolenic acid | C 18 | | 0.7 | | 0.4 | 5.2 |
| Hydroxy-oleic acid | C 18 | | | | 87.7 | |
| Arachidic acid | C 20 | | 0.2 | | 0.1 | 0.8 |
| Arachidic acid, mono-unsaturated | C 20 | | 0.7 | | 0.8 | 11.8 |
| Behenic acid | C 22 | | | | | 0.6 |
| Behenic acid, mono-unsaturated | C 22 | | | | | 25.0 |

EXAMPLES XI-XVII

Clear liquid soap solutions were prepared having the following compositions:

| Composition (% by weight) | XI | XII | XIII | XIV | XV | XVI | XVII | 0 |
|---|---|---|---|---|---|---|---|---|
| sodium oleate | 6 | 6 | 12 | 12 | 12 | 18 | 18 | 10 |
| sodium laurate | 4 | 4 | 8 | 8 | 8 | 12 | 12 | — |
| sodium tripolyphosphate | 8 | 15 | 15 | — | 7 | 10 | — | 2 |
| sodium nitrilotriacetate | — | — | — | 10 | 10 | — | 5 | — |
| water | 82 | 75 | 65 | 70 | 63 | 60 | 65 | 88 |

The last column (O) which is given for comparison shows the maximum solubility of sodium tripolyphosphate in an aqueous soap system outside the invention.

What is claimed is:

1. An aqueous liquid sodium soap solution containing from 20% to 45% by weight of a sodium soap consisting essentially of a mixture of (A) at least one sodium soap of $C_8$–$C_{14}$ saturated fatty acid and
(B) at least one sodium soap of fatty acids selected from the group consisting essentially of $C_{16}$–$C_{22}$ mono and $C_{16}$–$C_{22}$ di-unsaturated fatty acids and mixtures thereof, the ratio of A to B being from 4:1 to 1:4.

2. An aqueous liquid soap solution according to claim 1 in which soap (A) is derived from $C_8$–$C_{14}$ saturated fatty acids having a proportion of $C_8$–$C_{12}$ fatty acids of more than 50% by weight, and soap (B) is derived from $C_{16}$–$C_{22}$ mono- and/or di-unsaturated fatty acids having a proportion of $C_{18}$-mono-unsaturated fatty acids of more than 50% by weight.

* * * * *